United States Patent
Shalaby et al.

(10) Patent No.: US 8,691,235 B2
(45) Date of Patent: Apr. 8, 2014

(54) ABSORBABLE CRYSTALLINE POLYETHER-ESTER-URETHANE-BASED BIOACTIVE LUMINAL LINER COMPOSITIONS

(75) Inventors: Shalaby W Shalaby, Anderson, SC (US); David Ingram, Central, SC (US); Georgios T Hilas, Anderson, SC (US); Sheila Nagatomi, Seneca, SC (US)

(73) Assignee: Poly-Med, Inc., Anderson, SC (US)

( * ) Notice: Subject to any disclaimer, the term of this patent is extended or adjusted under 35 U.S.C. 154(b) by 820 days.

(21) Appl. No.: 12/798,458

(22) Filed: Apr. 5, 2010

(65) Prior Publication Data
US 2010/0255016 A1    Oct. 7, 2010

Related U.S. Application Data

(60) Provisional application No. 61/211,800, filed on Apr. 3, 2009.

(51) Int. Cl.
| | | |
|---|---|---|
| *A61K 39/00* | (2006.01) | |
| *A61K 31/496* | (2006.01) | |
| *A61K 31/4164* | (2006.01) | |
| *A61K 31/506* | (2006.01) | |
| *A61K 31/4196* | (2006.01) | |
| *A61K 31/04* | (2006.01) | |

(52) U.S. Cl.
USPC ............ 424/184.1; 514/256; 514/254.07; 514/399; 514/383; 514/422

(58) Field of Classification Search
USPC ......... 424/184.1; 514/254.07, 399, 256, 383, 514/422
See application file for complete search history.

(56) References Cited

U.S. PATENT DOCUMENTS

| | | | |
|---|---|---|---|
| 4,742,147 A | 5/1988 | Nichols | |
| 4,990,357 A | 2/1991 | Karakelle et al. | |
| 6,416,779 B1 * | 7/2002 | D'Augustine et al. | 424/430 |
| 2006/0286143 A1 * | 12/2006 | Shalaby et al. | 424/423 |
| 2009/0233887 A1 | 9/2009 | Shalaby | |

FOREIGN PATENT DOCUMENTS

| | | | | |
|---|---|---|---|---|
| WO | WO 81/0035 | * | 2/1981 | A61M 7/00 |
| WO | WO2006/017341 | * | 2/2006 | A61K 9/70 |

OTHER PUBLICATIONS

Gravert et al. Chem. Rev. 1997, 97, 489-509.*
Cohn et al. Biomaterials, vol. 27, Mar. 9, 2006 1718-1727.*
Rechichi et al, J. Biomed. Mater. Res., 2008, vol. 84-A, Iss 4, pp. 847-855.
Schubert et al, J. Biomed. Mater. Res., 1997, vol. 35-A, Iss 3, pp. 319-328.
Ward et al., J. Biomed. Mater. Res., 2008, vol. 77-A, Iss 2, pp. 380-389.

* cited by examiner

*Primary Examiner* — Anoop Singh
*Assistant Examiner* — Anna Falkowitz
(74) *Attorney, Agent, or Firm* — McCormick, Paulding & Huber LLP

(57) ABSTRACT

Bioactive hydroforming luminal liner compositions are formed of an absorbable crystalline amphiphilic polyether-ester-urethane dissolved in a liquid derivative of a polyether glycol that undergoes transformation into a tissue-adhering, resilient interior cover or liner for the controlled release of its bioactive payload at clinically compromised conduits in humans as in the case of bacteria- and yeast-infected vaginal canals, esophagi, and arteries following angioplasty.

12 Claims, No Drawings

ABSORBABLE CRYSTALLINE POLYETHER-ESTER-URETHANE-BASED BIOACTIVE LUMINAL LINER COMPOSITIONS

The present application claims the benefit of prior provisional application, U.S. Ser. No. 61/211,800, filed Apr. 3, 2009.

FIELD OF THE INVENTION

The present invention is directed to absorbable, crystalline, polyether-ester-urethane-based compositions that can be delivered to the luminal wall of a body cavity or conduit of the gastrointestinal tract, urinogenital or vascular systems to form a bioactive, adhering liner upon contacting the respective wet luminal surface, wherein the bioactivity of the liner is associated with the controlled release of at least one bioactive agent selected from the group consisting of antimicrobial, antiviral, immunosuppressant, antineoplastic, and anti-inflammatory agents. The bioactive luminal liners are applicable for use in treating vaginal and esophageal fungal infections and further in preventing vascular restenosis following angioplasty and treating urinogenital infections.

BACKGROUND OF THE INVENTION

Polyurethanes represent a main class of synthetic elastomers employed for long-term, medical implants as they present tunable chemical properties, excellent mechanical properties, good blood compatibility, and also can be designed to degrade in biological environments [A. Rechichi et al., *J. Biomed. Mater. Res.*, 84-A, 847 (2008)]. More specifically, polyether-urethane (PEU) and polyether-urethane-urea (PEUU) elastomers have long been considered ideal for use in many implanted devices, in spite of occasionally cited drawbacks [M. A. Schubert et al., *J. Biomed. Mater. Res.*, 35, 319 (1997); B. Ward et al., *J. Biomed. Mater. Res.*, 77-A, 380 (2008)]. Of the cited drawbacks are those associated with (1) the generation of aromatic diamines, which are considered to be toxic upon degradation of segmented copolymers made using aromatic diisocyanates for interlinking; (2) chain degradation due to oxidation or radiation degradation of the polyether component of segmented copolymers, and particularly those which encounter frequent mechanical stresses in the biological environment; and (3) chemical degradation in chemically and mechanically hostile biological environments of the urethane links of segmented copolymers and particularly those comprising reactive aromatic urethane linkages.

Liquid solventless, complex polymeric compositions, which thermoset at ambient temperatures through additional polymerization of a two-component system, wherein the first component comprises amine or acrylate-terminated polyurethanes or polyurethane-ureas and the second component comprises di- or polyacrylates have been described in U.S. Pat. No. 4,742,147. However, the prior art is virtually silent on self-standing PEU and PEUU liquid solventless compositions for use in pharmaceutical formulations and/or medical devices. Similarly, the prior art on polyether-urethanes is practically silent on hydroswellable (or water-swellable) systems, in spite of the fact that it addresses elastomeric, segmented, hydrophilic polyether-urethane-based, lubricious coating compositions based on aromatic diisocyanate and polyethylene glycol (U.S. Pat. No. 4,990,357)—it did not suggest a self-standing material for medical device applications. This prompted a study subject of a recent disclosure by one inventor of the instant invention and his coworkers (U.S. patent application Ser. No. 12/380,391). The latter disclosure dealt in general with hydroswellable, absorbable and non-absorbable, aliphatic, segmented polyurethanes and polyurethane-urea capable of swelling in the biological environment with associated increase in volume of at least 3 percent have more than one type of segments, including those derived from polyethylene glycol and the molecular chains are structurally tailored to allow the use of corresponding formulations and medical devices as carriers for bioactive agents, rheological modifiers of cyanoacrylate-based tissue adhesives, as protective devices for repairing defective or diseased components of articulating joints and their cartilage, and scaffolds for cartilage tissue engineering.

Most pertinent to the instant invention are certain composition and formulations described in U.S. patent application Ser. No. 12/380,391, which can be used as (1) injectable gel-forming liquid formulations for the controlled delivery of bioactive agents for treating periodontitis, nail infections, bone infections, a variety of bacterial and fungal infections, and different forms of cancers, and (2) in situ-forming, extrudable luminal liner for the controlled drug delivery at the luminal wall of vaginal canals and blood vessels. However, the use of these compositions as covers or liners on the luminal wall of vaginal canals, esophagi, and blood vessels may be less than optimum since the teaching of U.S. patent application Ser. No. 12/380,391 deals mostly with hydroswellable amorphous coatings, which may undergo excessive deformation and creep in presence of low levels of shear stresses. This prompted the study, subject of the present invention, which relates to a new class of absorbable crystalline polyether-ester-urethane-based compositions, which represent a substantial improvement over their amorphous analogs of the prior art, in terms of providing a set of balanced properties that support hydroformation into tissue-adhering liners that are not only resilient, but also resist deformation in the presence of shear forces.

SUMMARY OF THE INVENTION

Accordingly, the present invention is directed to a bioactive hydroforming luminal liner composition comprising at least one absorbable crystalline amphiphilic polyether-ester-urethane having a molecular weight of at least 10 kDa, preferably at least 20 kDa, more preferably at least 35 kDa, most preferably at least 50 kDa, and a heat of fusion exceeding 5 J/g, preferably exceeding 10 J/g, more preferably exceeding 20 J/g, most preferably exceeding 30 J/g, a liquid derivative of a polyether glycol and at least one bioactive agent selected from the group consisting of antimicrobial, antiretroviral, antiviral, antiretroviral, anti-inflammatory, antiproliferative, immunosuppressing, antineoplastic, and anesthetic agents, wherein the at least one absorbable crystalline polyether-ester-urethane is the reaction product of at least one polyalkylene glycol, end-grafted with at least one cyclic monomer selected from the group consisting of ε-caprolactone, p-dioxanone, a lactide, glycolide, 1,5dioxapan-2-one, trimethylene carbonate, and a morpholinedione. The resulting end-grafted product is further interlinked with a diisocyanate, wherein any unreacted isocyanate group is converted to a urethane group through reacting with an aliphatic alcohol, and wherein the absorbable crystalline polyether-ester-urethane is the reaction product of a polyethylene glycol having a molecular weight of 3 to 35 kDa end-grafted with at least one cyclic monomer selected from the group consisting of ε-caprolactone, p-dioxanone, a lactide, glycolide, 1,5dioxapan-2-one, trimethylene carbonate, and a morpholinedione. The resulting end-grafted product is further interlinked with at least one aliphatic diisocyanate selected from the group consisting of 1,4-tetramethylene diisocyanate, 1,4-bis(methylene isocyanato) cyclohexane, 1,6-hexamethylene diisocyanate, and lysine diisocyanate, and any unreacted isocyanate is converted to a urethane group through reacting with 2-propanal, and further wherein the at least one bioactive agent is an antifungal agent selected from the group consisting of ketoconazole, miconazole, voriconazole, and fluconazole. The respective antifungal formulation can be used for treating vaginal yeast infection in humans using an applicator kit for delivering the active formulation which includes a solid applicator in a tubular housing of slightly larger diameter wherein the applicator has clockwise, helical grooves 2 mm in width and depth and both the applicator and tubular housing are threaded at their ends to allow secure assembling of the kit.

A second major aspect of this invention deals with a bioactive hydroforming luminal liner composition comprising at least one absorbable crystalline amphiphilic polyether-ester-urethane having a molecular weight of at least 10 kDa, preferably at least 20 kDa, more preferably at least 35 kDa, most preferably at least 50 kDa, and a heat of fusion exceeding 5 J/g, preferably exceeding 10 J/g, more preferably exceeding 20 J/g, most preferably exceeding 30 J/g, a liquid derivative of a polyether glycol and at least one bioactive agent selected from the group consisting of antimicrobial, antiretroviral, antiviral, antiretroviral, anti-inflammatory, antiproliferative, immunosuppressing, antineoplastic, and anesthetic agents, wherein the at least one absorbable crystalline polyether-ester-urethane is the reaction product of at least one polyalkylene glycol, end-grafted with at least one cyclic monomer selected from the group consisting of ε-caprolactone, p-dioxanone, a lactide, glycolide, 1,5dioxapan-2-one, trimethylene carbonate, and a morpholinedione. The resulting end-grafted product is further interlinked with a diisocyanate, and any unreacted isocyanate group is converted to a urethane group through reacting with an aliphatic alcohol, and wherein the absorbable crystalline polyether-ester-urethane is the reaction product of a polyethylene glycol having a molecular weight of 3 to 35 kDa end-grafted with at least one cyclic monomer selected from the group consisting of ε-caprolactone, p-dioxanone, a lactide, glycolide, 1,5dioxapan-2-one, trimethylene carbonate, and a morpholinedione and again the resulting end-grafted product is further interlinked with at least one aliphatic diisocyanate selected from the group consisting of 1,4-tetramethylene diisocyanate, 1,4-bis(methylene isocyanato) cyclohexane, 1,6-hexamethylene diisocyanate, and lysine diisocyanate, and any unreacted isocyanate is converted to a urethane group through reacting with 2-propanal, and further wherein the at least one liquid derivative of a polyether glycol is selected from the group consisting of acylated polyethylene glycol, benzylated polyethylene glycol, o-alkylated polyethylene glycol, o-benzylated polyethylene glycol, acylated copolymers of ethylene and propylene oxide, benzylated copolymer of ethylene and propylene oxide and benzylated copolymer of ethylene and propylene oxide.

A third major aspect of the instant invention deals with a bioactive hydroforming luminal liner composition comprising at least one absorbable crystalline amphiphilic polyether-ester-urethane having a molecular weight of at least 10 kDa, preferably at least 20 kDa, more preferably at least 35 kDa, most preferably at least 50 kDa, and a heat of fusion exceeding 5 J/g, preferably exceeding 10 J/g, more preferably exceeding 20 J/g, most preferably exceeding 30 J/g, a liquid derivative of a polyether glycol and at least one bioactive agent selected from the group consisting of antimicrobial, antiretroviral, antiviral, antiretroviral, anti-inflammatory, antiproliferative, immunosuppressing, antineoplastic, and anesthetic agents, wherein the at least one absorbable crystalline polyether-ester-urethane is the reaction product of at least one polyalkylene glycol, end-grafted with at least one cyclic monomer selected from the group consisting of ε-caprolactone, p-dioxanone, a lactide, glycolide, 1,5dioxapan-2-one, trimethylene carbonate, and a morpholinedione, the resulting end-grafted product is further interlinked with a diisocyanate, and any unreacted isocyanate group is converted to a urethane group through reacting with an aliphatic alcohol, and wherein the absorbable crystalline polyether-ester-urethane comprising the reaction product of a polyethylene glycol having a molecular weight of 3 to 35 kDa end-grafted with at least one cyclic monomer selected from the group consisting of ε-caprolactone, p-dioxanone, a lactide, glycolide, 1,5dioxapan-2-one, trimethylene carbonate, and a morpholinedione, the resulting end-grafted product is further interlinked with at least one aliphatic diisocyanate selected from the group consisting of 1,4-tetramethylene diisocyanate, 1,4-bis(methylene isocyanato) cyclohexane, 1,6-hexamethylene diisocyanate, and lysine diisocyanate, and any unreacted isocyanate is converted to a urethane group through reacting with 2-propanal, and further wherein the at least one bioactive agent is an antibacterial agent selected from the group consisting of metronidazole, clindamycin, doxycycline, and tobramycin. The respective antibacterial formulation can be used for treating vaginal and esophageal bacterial infections in humans.

A clinically important aspect of this invention deals with the use of the subject polymers as carriers for treating (a) steroid-responsive dermatitis using hydrocortisone or triamcinolone; (b) septic arthritis and osteomyelitis using vancomycin or methylprednisolone; and (c) vaginal, esophageal or nail infection using ketoconazole, miconazole, terbinafine or voriconazole.

From a technological perspective, the antifungal and antibacterial formulation, subject of this invention, further include a method of preparation, sterilization, and packaging entailing the steps of (a) dissolving the crystalline polyether-ester-urethane in the liquid derivative of a polyether glycol; (b) heat-sterilizing the liquid solution; (c) mixing the sterilized liquid solution with the antifungal or antibacterial agent, under aseptic conditions; (d) transferring an aliquot of active formulation from step "c" to a pre-sterilized plastic tubular housing of the applicator and securing the applicator in the housing; (e) placing the assembled applicator kit from step "d" in a sealable clear plastic pouch; and (f) heat-sealing the plastic pouch from step "e."

From a clinical perspective, the intravaginal application of the antifungal and antibacterial formulation, subject of this invention requires an applicator kit for delivering the active formulation comprising a solid applicator in a tubular housing of slightly larger diameter wherein the applicator has clockwise, helical grooves 2 mm in width and depth, both the applicator and tubular housing are threaded at their ends to allow secure assembling of the kit. Meanwhile, a method for application of said antifungal formulation onto the mucosal lining of the vagina of a human entails the steps of (a) removing the applicator loaded with the liquid drug-loaded formulation; (b) inserting the applicator into the vaginal canal using a clockwise, inward movement; and (c) removing the applicator from the vaginal canal using a counter-clockwise, outward movement.

A fourth major aspect of this invention deals with a bioactive hydroforming luminal liner composition comprising at least one absorbable crystalline amphiphilic polyether-ester-urethane having a molecular weight of at least 10 kDa, preferably at least 20 kDa, more preferably at least 35 kDa, most preferably at least 50 kDa, and a heat of fusion exceeding 5 J/g, preferably exceeding 10 J/g, more preferably exceeding 20 J/g, most preferably exceeding 30 J/g, a liquid derivative of a polyether glycol and at least one bioactive agent selected from the group consisting of antimicrobial, antiretroviral, antiviral, antiretroviral, anti-inflammatory (steroidal and non-steroidal), antiproliferative, immunosuppressing, antineoplastic, and anesthetic agents, wherein the at least one bioactive agent is one or two agents capable of preventing restenosis following arterial angioplasty, and wherein preventing restenosis is effected by a combination of an anti-inflammatory agent and a second agent selected from the group consisting of antiproliferative, antineoplastic, immunosuppressing, and antimicrobial agents, and further, wherein the anti-inflammatory agent is naproxen, the antineoplastic agent is paclitaxel or curcumin and the immunosuppressing agent is rapamycin. From a clinical perspective, thee formulations require the use of an applicator kit, similar to those used in endovascular stent deployment, for delivering the active formulation comprising an inflatable inner catheter inside a blind catheter with multiple holes in the axial wall for the extrusion of the liquid formulation onto the luminal wall upon inflating the inner catheter. Meanwhile, a method of preparation, sterilization, and packaging the catheter components of the applicator kit, entailing the steps of (a) dissolving the crystalline polyether-ester-urethane in the liquid derivative of a polyether glycol; (b) heat-sterilizing the liquid solution; (c) mixing the sterilized liquid solution with the bioactive agent or agents under aseptic conditions; (d) transferring an aliquot of the active formulation from step "c" into the blind end of the outside catheter; (e) inserting the inflatable inner catheter inside the outer one up to the point preceding the holed zone of the blind catheter; and (f) incorporating the two-catheter kit into a modified deployment kit for endovascular stents.

DETAILED DESCRIPTION OF PREFERRED EMBODIMENTS

In a major aspect the present invention is directed to the treatment of vaginal and esophageal candidiasis. Vaginal Candidiasis (VC) is a common medical problem in women and is associated with discomfort, particularly due to a copious discharge, which is often accompanied by odor. Currently available treatments of yeast infection include (1) a systemic oral administration therapy; (2) use of topical creams; and (3) use of intravaginal suppositories which release the drug after melting or dissolving in the vagina. However, the systemic administration can lead to drug toxicity, while all other currently used forms for intravaginal administration are subject to uncontrolled leakage of the drug during the vaginal discharge, creating unsanitary conditions and discomfort while resulting in unpredictable bioavailability of the drug. Esophageal candidiasis (EC) is another form of fungal infection caused in most cases by a candida species and results in sore throat and difficulty in swallowing. This infection is becoming more serious with the growing number of HIV patients who are highly susceptible to yeast infection. The orally administered treatment options of EC using oral formulations are particularly effective in HIV patients. However, there have been concerns about the clinical relapse in these patients, which is dependent upon the degree of immunosuppression apart from the potential hepatotoxicity associated with high or prolonged doses of orally administered drugs. Clinical shortcomings of the current treatments of VC and EC evoked the need to explore the development of topically administered drug delivery systems that are not affected by the aqueous vaginal discharge in the vagina and food transport in the esophagus, in part because of its good adhesion to the vaginal and esophageal linings to provide predictably modulated release of the drug. The need for such a novel drug delivery system prompted the pursuit of the study, subject of the present invention.

Accordingly, the invention is directed to a new class of polyether-ester-urethane-based compositions comprising at least one crystalline amphiphilic absorbable polyether-ester-urethane and at least one bioactive agent dissolved in a liquid derivative of a polyalkylene glycol. The chemical composition of the polyether-ester-urethane (PEEU), polyalkylene glycol derivative, and the bioactive agents and their relative concentrations in these compositions can be controlled to achieve balanced properties so as to (1) provide the proper viscosity to allow their facile delivery to the application site using existing deployment equipment or modifications thereof; (2) allow a timely hydroformation (i.e., phase separation in the presence of an aqueous environment, as in biological sites) into tissue adhering liner (or cover) that is biomechanically compatible with the lining of body cavities or canals as in the case of the vagina, esophagus, and blood vessels—hydroformation is effected by the migration of the polymeric solvent (with simultaneous phase separation of the PEEU to form a liner) and liner adhesion to the interior surface of the luminal wall is promoted by the highly hydrophilic polyether component of the polyether-ester-urethane; (3) form a crystalline liner exhibiting resilience and controlled dimensional stability by virtue of the segmented amphiphilic nature of the PEEU chain and the presence of quasi-crosslinks (presented by the crystalline fraction and association of the urethane segments), respectively; (4) be loaded with at least one type of bioactive agent, depending on the intended use of the bioactive compositions by virtue of having components which can be selected to dissolve or disperse a broad range of bioactive agents exhibiting different solubility parameters; and (5) allow achieving controllable release profiles of the different bioactive agents at the application sites by virtue of having PEEU compositions capable of having variable hydrophilic/hydrophobic ratios to be in concert with the desired modes of drug release. Further illustrations of the present invention are provided by the following examples:

EXAMPLE 1

Synthesis and Characterization of an Absorbable, Crystalline Polyether-ester-Urethane (C-PU): General Method For an initial charge, poly(ethylene glycol) (PEG-1000) ($M_w$=1000 Da) was added to a 250 mL, 2-neck, round-bottom flask. The contents were heated at 100° C. under reduced pressure for 1 hour and then purged with dry nitrogen. A mechanical stir rod was installed with a Teflon bearing assembly and the contents were heated to 100° C.-110° C. while stirring. A second charge, consisting of 1-lactide and glycolide was added and stirred at 120 RPM until the reaction mixture achieved one phase. A third charge, Tin(II) 2-ethyl hexanoate, was then added in a 0.2M solution in toluene. The reaction solution was then heated at 100° C. until near complete monomer conversion was achieved. The polymer was then cooled to 100° C. and diisocyanatohexane was added. The solution was then stirred at 100° C. for at least one hour until the isocyanate reacted completely. After interlinking the polymer was heated at 100° C. for 2.5-3.0 hours and then was dissolved at 55-67° C. in tetrahydrofuran (THF). After dissolution of the polymer in the THF, 2-propanol was added to react with any isocyanate end-groups and the solution was stirred for 1 hour. The resulting polymer was isolated by evaporating the solvent under reduced pressure and characterized for identity (IR), molecular weight (GPC), and thermal properties (DSC).

EXAMPLE 2

Synthesis and Characterization of Two Typical Absorbable, Crystalline Polyether-Ester-Urethanes, C-PU-1 and C-PU-2

Poly-ester-urethanes C-PU-1 and C-PU-2 were prepared using the method of Example 1. The poly(ethylene glycol) used in C-PU-1 and C-PU-2 had a molecular weight of 1000 Dalton. For Poly-ester-urethanes C-PU-1 and C-PU-2, 0.025 and 0.025 moles of poly(ethylene glycol), 0.46 and 0.48 moles of 1-lactide, 0.08 and 0.05 moles of glycolide, $6.71 \times 10^{-5}$ and $6.64 \times 10^{-5}$ moles of tin(II) 2-ethyl hexanoate, and 0.017 and 0.017 moles of 1,6-diisocyanatohexane were used, respectively. Polymers C-PU-1 and C-PU-2 were characterized for molecular weight by GPC using dichloromethane as the mobile phase which resulted in $M_n$ of 18 and 22 kDa, $M_w$ of 38 and 133 kDa, Mp of 24 and 63 kDa, and PDI of 2.2 and 6.1, respectively. Six mg samples of C-PU-1 and C-PU-2 were annealed in 5 mL glass vials submerged in a 70° C. oil bath for 1.75 hours, equilibrated in the DSC apparatus for 5 minutes at 20° C. upon removal from the bath, and heated to 220° C. at a rate of 20° C./min to determine the thermal properties. This resulted in melting temperatures/heats of fusion ($T_m/\Delta H$) of 90.9° C./7.9 J/g and 92.5° C./16.3 J/g for C-PU-1 and C-PU-2 respectively.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A bioactive hydroforming luminal liner composition comprising:
   at least one absorbable crystalline amphiphilic polyether-ester-urethane comprising at least one polyalkylene glycol end-grafted with at least one cyclic monomer selected from the group consisting of ε-caprolactone, p-dioxanone, a lactide, glycolide, 1,5dioxapan-2-one, trimethylene carbonate, and a morpholinedione to form an end-grafted product, wherein polyether-ester is interlinked with a diisocyanate to form a polyether-ester-urethane with an alternating structure (C-[A-B-A])m, wherein C is derived from the diisocyanate, A is the polyester, and B is the polyether, wherein the molar ratio of cyclic monomer to polyalkylene glycol is about 20:1, the molar ratio of polyalkylene glycol to diisocyanate is about 1.5:1, and any unreacted isocyanate group is converted to a urethane group through reaction with an aliphatic alcohol, said polyether-ester-urethane having a molecular weight of at least 10 kDa and a heat of fusion greater than 5 J/g;
   a liquid derivative of a polyether glycol;
   and at least one bioactive agent selected from the group consisting of antimicrobial, antiretroviral, antiviral, antiretroviral, anti-inflammatory, antiproliferative, immunosuppressing, antineoplastic, and anesthetic agents.

2. A bioactive hydroforming luminal liner composition as in claim 1 wherein the absorbable crystalline polyether-ester-urethane comprises a polyethylene glycol having a molecular weight of 3 to 35 kDa end-grafted with at least one cyclic monomer selected from the group consisting of ε-caprolactone, p-dioxanone, a lactide, glycolide, 1,5dioxapan-2-one, trimethylene carbonate, and a morpholinedione, and further interlinked with at least one aliphatic diisocyanate selected from the group consisting of 1,4-tetramethylene diisocyanate, 1,4-bis(methylene isocyanato) cyclohexane, 1,6-hexamethylene diisocyanate, and lysine diisocyanate, wherein any unreacted isocyanate is converted to a urethane group through reaction with 2-propanol.

3. A bioactive absorbable hydroforming luminal liner composition as in claim 1 wherein the at least one bioactive agent comprises an antifungal agent selected from the group consisting of ketoconazole, miconazole, voriconazole, and fluconazole.

4. A bioactive hydroforming luminal liner composition as in claim 1 wherein the at least one liquid derivative of a polyether glycol is selected from the group consisting of acylated polyethylene glycol, benzylated polyethylene glycol, o-alkylated polyethylene glycol, o-benzylated polyethylene glycol, acylated copolymers of ethylene and propylene oxide, benzylated copolymer of ethylene and propylene oxide and benzylated copolymer of ethylene and propylene oxide.

5. A bioactive, hydroforming luminal liner composition as in claim 3 as an antifungal formulation for treating yeast infection in humans, the yeast infections selected from the group consisting of vaginal yeast infections and esophageal yeast infections.

6. A bioactive, hydroforming luminal liner composition as in claim 1 wherein the at least one bioactive agent comprises an antibacterial agent selected from the group consisting of metronidazole, clindamycin, doxycycline, and tobramycin.

7. A bioactive, hydroforming luminal liner composition as in claim 6 as an antibacterial formulation for treating bacterial infection in humans, the bacterial infections selected from vaginal bacterial infections and esophageal bacterial infections.

8. A bioactive, hydroforming luminal liner composition as in claim 5 further including an applicator kit for delivering the active formulation comprising a solid applicator in a tubular housing of larger diameter, wherein the applicator has clockwise, helical grooves of about 2 mm in width and depth, and wherein both the applicator and tubular housing are threaded at the ends to allow secure assembling of the kit.

9. A bioactive, absorbable, hydroforming luminal liner composition as in claim 5 further comprising a method of preparation, sterilization, and packaging entailing the steps of:
   a) dissolving the crystalline polyether-ester-urethane in the liquid derivative of a polyether glycol;
   b) heat-sterilizing the liquid solution;
   c) mixing the sterilized liquid solution with the antifungal agent, under aseptic conditions;
   d) transferring an aliquot of active formulation from step "c" to a pre-sterilized plastic tubular housing of the applicator and securing the applicator in a housing;
   e) placing the assembled applicator kit from step "d" in a sealable clear plastic pouch;
   f) heat-sealing the plastic pouch from step "e.".

10. A bioactive, absorbable, hydroforming luminal liner composition as in claim 6 further comprising a method of preparation, sterilization, and packaging entailing the steps of:
   a) dissolving the crystalline polyether-ester-urethane in the liquid derivative of a polyether glycol;
   b) heat-sterilizing the liquid solution;
   c) mixing the sterilized liquid solution with the antibacterial agent, under aseptic conditions;
   d) transferring an aliquot of active formulation from step "c" to a pre-sterilized plastic tubular housing of the applicator and securing the applicator in a housing;
   e) placing the assembled applicator kit from step "d" in a sealable clear plastic pouch;
   f) heat-sealing the plastic pouch from step "e.".

11. A bioactive, hydroforming luminal liner composition as in claim 8 further including a method for application of said antifungal formulation onto the mucosal lining of the vagina of a human entailing the steps of
   a) removing the applicator loaded with the liquid drug-loaded formulation;
   b) inserting the applicator into the vaginal canal using a clockwise, inward movement; and
   c) removing the applicator from the vaginal canal using a counter-clockwise, outward movement.

12. A bioactive hydroforming luminal liner composition as in claim 1 wherein the polyalkylene glycol is polyethylene glycol, the at least one cyclic monomer is selected from the group consisting of a lactide and glycolide, the molar ratio of cyclic monomer to polyalkylene glycol is 21.6:1, the molar ratio of polyethylene glycol to diisocyanate is 1.47:1, and any unreacted isocyanate group is converted to a urethane group through reaction with an aliphatic alcohol.

* * * * *